United States Patent [19]

Harmening-Pittiglio

[11] 4,390,619

[45] Jun. 28, 1983

[54] LEUKOCYTE OR PLATELET STORAGE USING ION-EXCHANGE RESINS

[75] Inventor: Denise Harmening-Pittiglio, Silver Spring, Md.

[73] Assignee: James Clifford Haight, Gaithersburg, Md.

[21] Appl. No.: 306,322

[22] Filed: Sep. 28, 1981

[51] Int. Cl.³ .............................................. A61K 35/14
[52] U.S. Cl. ......................................... 435/2; 424/78; 424/79; 424/81; 424/101
[58] Field of Search ............................ 424/101; 435/2

[56] References Cited

U.S. PATENT DOCUMENTS

| 4,112,070 | 9/1978 | Harmening | 435/2 |
| 4,148,878 | 4/1979 | Nelson | 424/101 |
| 4,199,954 | 4/1980 | McGill | 424/101 |

*Primary Examiner*—Sam Rosen
*Attorney, Agent, or Firm*—Haight & Associates

[57] ABSTRACT

A method of storing and preserving the shelf life of leukocytes or platelets suitable for transfusion is extended by maintaining viable platelets having adequate ATP and pH levels using an insoluble polymer material as a source of weakly basic buffer ions during the storage period.

20 Claims, 10 Drawing Figures

LEUKOCYTE OR PLATELET STORAGE USING ION-EXCHANGE RESINS

DESCRIPTION OF THE INVENTION

1. Technical Field of the Invention

This invention relates to an improved leukocyte or platelet storage method and composition. More particularly, this invention relates to such improvements in the storage of leukocytes or platelet concentrates and of packed platelets suitable for transfusion.

2. Background Art

Not only are preservative solutions of profound importance in the maintenance of red cell function and viability, as described in U.S. Pat. No. 4,112,070 but they also have a direct influence on leukocyte and platelet function and viability. This is an important issue to examine because of the expanding use of component therapy for transfusion practices and especially because of the large number (2.2 million in 1979) of platelet concentrates (PC) transfused annually. While the following discussion emphasizes platelet storage, it will be appreciated that the cellular organelles of platelets are present in leukocytes and metabolic pathways of platelets and leukocytes are accordingly similar. Existing controversies regarding platelet storage have resulted in attempts to reduce discrepancies regarding the hemostatic effectiveness of transfused PC. In the 1950's, platelet transfusions were given as freshly drawn whole blood or platelet-rich plasma. These platelets disappeared within 4–5 days after injection into the blood stream of patients with thrombocytopenia secondary to marrow failure. An alternative method was to prepare platelet concentrates (PC). A unit of blood was drawn into a plastic bag containing an anticoagulant and centrifuged at 4° C. to prepare platelet-rich plasma (PRP). The PRP was centrifuged a second time and the excess plasma expelled to prepare PC.

Current health regulations generally permit platelets to be stored for three days. Storage conditions, by necessity, themselves cause alterations in the metabolism and function of platelets. Initial pH, temperature of storage, total platelet count, volume of plasma, duration of storage, agitation during storage and hydrogen ion accumulation are some of the factors known to influence the storage of platelets.

A number of other interrelated variables can also affect platelet viability and function during storage, namely, the anticoagulant used for blood collection, the method used to prepare platelet concentrates and the composition, surface area, and thickness of the walls of the storage container.

A major advance in the development of platelet storage occurred with the important discovery which demonstrated with survival studies that the optimum storage temperature for platelets was 22° C. rather than 4° C. 4° C. stored platelets are associated with an irreversible disc to sphere transformation. All of the platelets assume a spherical shape after only 10 minutes of 4° C. storage. Some platelets return to the disc form upon warming at 37° C. However, when stored for several hours at 4° C., platelets do not return to their disc shape upon rewarming and are irreversibly sphered. This spherical change is associated with an increase of approximately 15–50% in platelet volume, and is a direct result of loss of circumferential bands of platelet microtubules. Upon rewarming, microtubles do reassemble but are randomly dispersed throughout the cytoplasm of the platelet. This loss of shape associated with 4° C. storage is probably a result of microtubule disassembly which may also be a major contributor to decreased survival of platelets sotred at 4° C. The major objection to 4° C. stored platelets is their shortened life span after reinfusion, and their marked decrease in survival after only 18 hours of storage.

In light of these developments, platelet concentrates are now prepared and store at 22° C. However, even 22° C. storage for platelets has several disadvantages. One major difficulty is the regulation of pH. Virtually all units of PC demonstrate a decrease in pH from their initial value of 7.0. This decrease is primarily due to the production of lactic acid by platelet glycolysis and to a lesser extent to accumulation of $CO_2$ from oxidative phosphorylation. As pH falls from 6.8 to 6.0, the platelets progressively change shape from discs to spheres. In this pH range, the change of shape is reversible if the platelets are resuspended in plasma with physiologic pH. However, if the pH falls below 6.0, a further irreversible change occurs which renders the platelets nonviable after infusion in vivo.

The present goal of platelet preservation is to prevent this change in pH. Apparently, oxygen supply to the platelets within the plastic bag is also intimately related to pH maintenance. If the supply is sufficient, glucose will be metabolized oxidatively resulting in $CO_2$ production, which diffuses out of the plastic walls of the PC container. If the supply of oxygen is insufficient, glucose will be metabolized anaerobically, resulting in the production of lactic acid, which must remain within the container and thus lowers the pH. The oxygen tension within the container is governed by several factors: the concentration of platelets which consume oxygen, the permeability of the plastic wall of the PC, the surface area of the container available for gas exchange, and the type of agitation utilized, since this facilitates gas exchange. Federal regulations require that some form of gentle agitation be used (Federal Register, 1975).

The only variable which the blood bank can modulate is the concentration of platelets. PC with a platelet count greater than $1.6 \times 10^6$ per ul commonly show evidence of inadequate oxygenation and a decline in pH over a 72 hour period. For this reason many blood banks now favor a PC plasma volume of 50 ml. This is the maximal value permitted by current regulations. Although this is a large volume for clinical use, especially in terms of pediatric patients, it does minimize the platelet concentration. Studies have indicated that oxygenation can be maintained by using a container with increased oxygen permeability. Future investigation of platelet preservation may lie in the development of more permeable plastics and new approaches to control of pH. However, all research is aimed at increasing the storage time of platelets while also maintaining platelet viability and function.

DISCLOSURE OF THE INVENTION

It has now been found that the in vivo shelf life of blood platelets can be extended beyond those currently attainable in the prior art by providing a storable, transfusable composition of matter comprising metabolizing platelets in an in vitro environment capable of supporting platelet metabolism having incorporated therein a water-insoluble polymer containing releasable weakly basic buffer ions capable of continuously supplying said buffer to the platelets.

Accordingly, it is a general object of the present invention to provide a platelet storage system substantially free of the above-indicated disadvantages of the current state-of-the-art.

Another object of the present invention is to provide a platelet storage system which extends the shelf-life of stored platelets while simultaneously maintaining cellular viabilty.

A further object of the present invention is to provide a platelet storage system which promotes the preservation of the platelet morphology.

An additional object of the present invention is to provide a platelet storage system which buffers the pH of stored platelets.

A more particular object of the present invention is to provide a platelet storage system which extends the functional life of platelets.

Yet another object of the present invention is a platelet storage and preservation system in which shelf-life extending additives can easily be removed prior to transfusion.

Upon study of the specification and appended claims, further objects, features and advantages of the present invention will become more fully apparent to those skilled in the art to which this invention pertains.

BRIEF DESCRIPTION OF DRAWINGS

The above and other objects, features, and advantages of the present invention will become more fully apparent to those of ordinary skill in the art to which this invention pertains from the following discussion, taken in connection with the annexed drawing of FIGS. 1 through 10, which are photomicrographs of human blood platelets taken by electron microscopy at various storage intervals in accordance with the examples that follow, and in which.

BEST MODE FOR CARRYING OUT THE INVENTION

Briefly, the above and other objects, features and advantages of the present invention are attained in one aspect thereof by providing living leukocytes, especially platelets, stored in vitro with a water-insoluble polymer containing releaseable buffer ions for supplying a physiologically acceptable, continuous source of metabolizable ions to said leukocytes in an amount and at a rate sufficient to maintain both pH and ATP levels suitable for transfusion. The buffer source is separable by physical as opposed to chemical techniques, preferably by simple filtration, decantation, or enclosure by semipermeable membranes.

DETAILED DISCUSSION

In accordance with the present invention, it has been found that insoluble polymeric material can be employed as a continuous source of a slightly alkaline buffer, preferably an inorganic buffer such as phosphate ions, particularly bicarbonate and/or di-basic phosphate, in storage and shelf-life extension of leukocytes or platelets. By providing means for sustained release of weakly basic buffer ions, pH, ATP levels, and cellular morphology can be maintained at values sufficiently high for transfusion purposes for a period of time of at least 7 days.

While not wishing to be bound by any theory of the invention, it is believed that both the buffer source and the continual release thereof in a leukocyte or platelet storage system are essential to attain the objects of the present invention. For example, the use of a weakly basic buffer alone without providing means for the systained, gradual release thereof does not achieve the desired results. By using a resin system as a continuous source of buffer ions, additional chemical additives are not required and the physiologically acceptable resin particles can be physically separated by being filtered out at the time of transfusion. Furthermore, resin particles having a tendency to adsorb bacteria from solutions can be employed as the buffer source, thereby minimizing the risk of septicemia acquired in the course of a transfusion.

It will be apparent to those skilled in the art to which the present invention pertains that a number of techniques can be employed to provide means for gradual release of buffer in accordance with present invention, e.g. microencapsulation, differentially degradable coatings, etc. However, presently preferred as a source of continually releasing buffer is a weakly basic anion exchange resin which has been equilibrated with the weakly basic buffer ion. Preferred ion exchange resins have a macroreticular bead structure containing many large, discrete pores which facilitate maximum ion diffusion. Because the organic framework is insoluble in all common laboratory solvents and chemically inert, it is readily separated from platelet concentrates prior to transfusion. Anion exchange resins, i.e., those possessing functional groups which can undergo reactions with anions in a surrounding solution, particularly weakly basic anion exchange resins, are preferred. For use in the platelet storage system of the present invention, such resins which have the additional properties of adsorbing acids from organic reaction mixtures, exchanging anions in a slightly acidic media, a high exchange capacity, low swelling properties and a tendency to adsorb bacteria from the surrounding solution are particularly advantageous. One such resin is commercially available under the trade name of Amerlite IR-45 from Rohm & Haas Company, a weakly basic, polystyrene-polyamine type anion exchange resin having a styrene-divinylbenzene matrix. The hydroxyl ionic form can be replaced with a metabolizable phosphate ionic group by simple equilibration, with any desired concentration of metabolizable phosphate in solution, e.g. using 1 M dibasic phosphate. The anion exchange resin may be used alone or in combination with other anion and/or cation exchange resins suitable for the intended purpose.

As the particles can circulate freely in storage bags and be filtered out at the time of transfusion, they are physically separable and especially convenient for use in platelet preservation.

With respect to the functionality of the ion exchange resin employed, polyamine functionality is preferred to the weakly basic anion exchange resins, the only presently known criteria being that the resin in its free base form must be suitable for the adsorption of acids from a weakly acidic organic mixture. The macroreticular structure is chemically stable and regenerable, and the functionality of polyamine anion exchange resins is suitable for exchanging hydroxyl for dibasic phosphate ions therein. A large number of such resins are commercially available, and include but are not limited to polystryrene-divinylbenzene polyamine functionalities such as Amberlite IRA-93, Stratabed 93, Amberlite IRA-94, Amberlite XE-270, Amberlite XE-299 and Amberlite IR-45. Phenolic polyamine weakly basic resins can be employed, e.g. Amberlite IRP-58M and the parent resin, Amberlite IR-4B. Likewise, acrylic ester anion exchange resins such as Amberlite ZAD-7, XAD-8, XE-236 and IRA-68 can be employed. Furthermore, the "condensate" type weakly basic anion exchange resins such as those sold under the trade names Amberlite IRA-47, IRA-47S and IRA-49 are also suitable, provided they meet the above criteria. "Amberlite" is a registered trademark of Rohm & Haas Co., USA. While the insoluble bead form is preferred because of the ease of subsequent separation, suitable resins can be employed in the gel form if appropriate precautions are taken in separation from the platelet concentrates prior to transfusion.

In order to provide a suitable, long-term source of buffer such as divalent inorganic phosphate ions, the anion exchange resin is equilibrated with a solution of the desired buffer ions using conventional techniques. The strength of the buffer solution employed and the length of time required for equilibration wil vary somewhat, as is known to those skilled in the art, depending on the particular physical and chemical properties of the specific anion exchange resin to be used. While the examples used herein employ divalent phosphate ion as the buffer, the principles of this invention are equally applicable to other equivalent buffers. Unlike the metabolism of erythrocytes, platelets appear to metabolize phosphate ions very slowly if at all. The mechanism of the present invention thus appears to be more directly related to pH control in the storage media, for which a wide variety of other buffers are suitable provided they are non-toxic to metabolizing platelets, e.g., by causing platelet aggregation or membrane damage or by chelating the calcium ions needed for platelet functionality. The buffer must, of course, be slightly alkaline, e.g. bicarbonate, and can be used alone or in combination with other similar buffers. The pH of such buffer is generally 7.2-11, preferably about 8-10. As previously indicated, the particular nature of the resin is not critical, so long as it meets the criteria of both acting and a reservoir for buffer ions and does not leave behind any physiologically unacceptable residues or byproducts. Any inert, physiologically compatable anion exchanger containing some form of a phosphorylated functional group will be suitable.

During seven days of storage of platelet concentrates (PC) at double the usual concentration of platelets in standard Fenwal PVC containers, a marked decrease in pH from baseline was observed in the control presumably as a result of the production of lactic acid through the glycolytic pathway as well as $CO_2$ production through the Krebs cycle. After 3 days the pH was 5.8, a level at which platelets are felt to be nonviable. The greatest $O_2$ consumption, $CO_2$ production, $HCO_3^-$ depletion and pH decrease was observed during the first 24 hours. These are similar to observations made by others during preservation of platelet concentrates with high platelet counts (Murphy et al, 1975). It is presumed that the increased platelet concentration results in an increased lactic acid production by the Pasteur effect with a high $CO_2$ production, which exceeds the capacity for its diffusion across the standard plastic containers. By the third day when pH has fallen below 6.0, a decrease in the consumption of $O_2$ and production of $CO_2$ was noted due to the decrease in viability of the stored platelets. Simultaneously striking changes in the morphology of the platelets were observed, which after 3 days of preservation reached 50% of the initial morphology score values with almost complete loss of discoid shape accompanied by marked degranulation.

In association with the decrease of pH after 24 hours and 3 days, striking decreases in the total amount of ATP per platelet to 80% and 19% were observed, respectively. From previous observations of platelet concentrates stored at +4° C. and +22° C., it is well known that the reduction of the total ATP level is secondary to the degradation of metabolic ATP to hypoxanthine. It has previously been shown that with a total ATP decrease of only 10% during 24 hours of storage, themetabolically active ATP is reduced by 40-50%. It is likely therefore that close to total depletion of metabolically available ATP occurred in the control platelets. This might well account for the observed deterioration of in vitro platelet function, as ATP is essential for such roles in hemostasis as platelet adhesion, platelet "release reaction", and platelet aggregation.

Platelets do have the ability to produce ATP by glycolysis and by mitochondrial oxidative phosphorylation. In the resting platelet mitochondrial metabolism is responsible for more than half of the metabolic ATP pool; the same applies to leukocytes.

As the contractile processes are ATP-dependent since phosphorylation of specific contractile protein is necessary for platelet activation, it is probable that some ATP must also be consumed in processes related to the onset of platelet function. Increased ATP turnover continues for several hours even after aggregation and secretory reactions are complete. This appears to be attributed also to alterations in adenine nucleotide balance.

The amount of adenine nucleotides released by thrombin decreased to 45% after 24 hours and to 0% after three days of preservation, consistent with these proposed hypotheses. Changes in membrane receptors for thrombin which have been demonstrated in platelets which have been drastically altered by storage, could also have contributed to the decreased responsiveness to thrombin.

Contrary to the values obtained in control platelets the total amount of ATP during the first 24 hours of preservation with resin system was maintained at baseline levels. This could be accounted for by an incorporation of phosphate anions released from the resin via R-5-P (ribose-5-phosphate) to PRPP (phosphoribosyl-1-pyrophosphate). However, AMP and R-5-P incorporated $p^{32}$-orthophosphate at a very slow rate, indicating very low or absent de novo synthesis of adenine nucleotides by platelets. Another explanation for the maintenance of the ATP levels is maintenance of adequate pH by the resin, which by enhancing the enzyme activity of glycolytic pathway—especially hexokinase and phosphofructokinase—allowed greater glucose utilization during the storage period. Although the pH did not change appreciably during the whole 7 day period of storage with 1 gram of resin, the total ATP level after the third and seventh day of preservation was still 77% and 56% of the baseline level respectively.

The ability of platelets stored with resin to maintain total ATP at 96–100% of normal levels during the first 24 hours was associated with continued responsiveness of the platelets to extracellular stimuli. Further declines in release despite only modest declines in total ATP levels could have been due to more profound decreases in metabolically available ATP, as well as membrane receptor alterations.

The addition of the resin markedly enhanced the buffering capacity of the system even with the high concentration of platelets used. The use of 1 gram resin kept the pH of platelet concentrates at 7.0 during the seven days, comparable to baseline levels. The use of resin was associated with a low bag $pO_2$ thru the 7th day, reflecting the continued presence of metabolically active platelets.

The fluctuation of $pO_2$ levels in PC has been found to be inversely proportional to platelet count in PCV containers. Therefore, since double quantities of PC were used, since one would expect the $pO_2$ to be low if the platelets are viable because of the high platelet count. The data demonstrate near zero levels of $pO_2$ in the PC with resin during the first three days of storage indicating viable platelet metabolism by this $O_2$ consumption. It has been known since 1911 that platelets consume oxygen. The existence of the Pasteur effect in platelets, which is linked to oxidative phosphorylation, has likewise been well-documented. The reduction of glycolysis by 50% with aerobiosis when platelets are in the presence of glucose suggests an essential role of mitochondria in platelet functionality. Platelet energy metabolism in the inactivated resting state has been estimated to be 50% glycolysis and 50% TCA cycle. In the activated state platelets revert their energy metabolism to approximately 80% glycolysis and only 20% TCA. Therefore, $pO_2$ levels could give an indication of the metabolic activity of stored inactivated platelets reflecting mitochondrial function. Loss of energy producing metabolism in the stored platelets would then be reflected in a rise in $pO_2$ and loss of $O_2$ consumption by platelet mitochondria.

In the control bags, $pCO_2$ levels dramatically rose in the first day of storage as opposed to the bags stored with resin. This represents active platelet energy metabolism of mitochondrial oxidation leading to a build-up of $CO_2$ levels and a drop in pH. Distinctively higher $pCO_2$ levels have been found with higher platelet counts; therefore, in platelet concentrate with higher platelet counts, pH depression would be due not only to increased production of lactic acid, but also to increased production of $CO_2$. In contrast, platelet concentrate stored with resin demonstrated much lower levels of $CO_2$ during the first day of storage. This may be due to an innate ability of the resin particles to bind $CO_2$. By the third day of storage, $pCO_2$ levels in the control bags decline to lower levels, probably reflecting the escape of $CO_2$ through the plastic containers. By the seventh day of storage, $CO_2$ levels in the control bags reach near zero levels, indicating a loss of energy metabolism through mitochondrial oxidation. In contrast, platelet concentrate stored with resin for 7 days still yield substantial levels of $CO_2$ indicating active metabolic production through the tricarboxylic acid cycle (TCA). These fluctuations in $pCO_2$ levels in platelet concentrate stored with resin are reflected in maintenance of pH around 7.0 during seven days of storage. In the control, bicarbonate measurements decline to near zero levels by the third day of storage. This depletion occurs due to the buffering of the acid produced during the storage period. In contrast, bicarbonate levels of platelet concentrates stored with resin maintain at least 40% of initial levels after seven days of storage. This maintenance of bicarbonate levels with the resin system is due to the additional phosphate buffering capacity of the resin.

Maintenance of the pH at 7.0 by the resin resulted in improved morphology of preserved platelets with maintenance of discoid shape and microtubles for 3 days, even at double the normally used platelet concentration. Even after 7 days of storage, the majority of platelets were still granulated and morphologically intact. Whether platelets stored under these conditions for 7 days could circulate post transfusion is speculative although there does appear to be a good relationship between post transfusion recovery and platelet morphology in other experimental conditions.

In comparison to one gram, the use of two grams of resin during the same conditions of platelet concentrate preservation produced higher pH values between 7.32 and 7.4 during the seven days of storage. This was probably the effect of greater combining with $CO_2$ by resin molecules which resulted in lower $pCO_2$ during the whole preservation period. This binding of $CO_2$ by the resin is also illustrated by the marked differences in bag $pCO_2$ between the control and resin bags during the first 24 hours of storage, i.e. the period of time during which the platelets were most metabolically active and produced the greatest amounts of $CO_2$. The $HCO_3$ level was also highest after seven days of platelet preservation when two grams of resin was used. This may reflect the increased buffering of the resin with relative "sparing" of the $HCO_3$ buffer. However, no improvement was observed in platelet count, the total ATP level, release of adenine nucleotides or $pO_2$ tension when two grams of resin were used in comparison to the results obtained with one gram of resin.

Disc-to-sphere transformation, degranulation possibly due to aggregation, and the release reaction have been noted in platelets stored at higher pHs. In the present experiments the morphology, as judged by phase microscopy, was similar in the 1 and 2 gram resin bags at 3 and 7 days. Electron micrographs were not done in the 2 gram preparations and it is possible that more subtle changes due to the higher pH were not detected.

This study on the effect of the resin on the metabolism and morphology of platelets during long term storage at ambient temperature shows the importance and benefit of maintenance of higher pH due to the removal of lactic acid and $CO_2$ metabolites from the plasma which was associated with an increase in the ATP level of these cells. Although the mechanism of the ATP increase is not clear, the use of the resin charged phosphate anion opens a number of new options in the area of platelet preservation.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Preparation of Platelet Concentrate (PC)

PC from ABO and Rh identical random donors were prepared by the double plasmapheresis method using ACD-A as an anti-coagulant. The PC were prepared in final volumes of 20 ml (i.e. twice the normal concentration) in an effort to maximally "stress" the preservative capability of the resin. Units of PC from three to four donors were then pooled and centrifuged at 180 g for three minutes to remove residual leukocytes and erythrocytes. Forty ml. aliquots of the suspension were then transferred to plastic blood bags with or without (control) ion exchange resin.

Both 300 ml Fenwal (PL-146 Plastic) and Cutter Transfer Bags (CL 3,000 plastic) were utilized. The bags were initially opened, filled with one or two grams of Amberlite IR-45 ion exchange resin, sealed, and vapor sterilized. The resin had been charged with dibasic phosphate as previously described in U.S. Pat. No. 4,112,070. Bags with or without resin were studied during seven days of storage at room temperature (20°-24° C.) with constant horizontal agitation at approximately 70 to 80 cycles per minute. Thus, platelets and the inert resin beads, which are approximately 400μ in diameter were continually mixed in free suspension with each other. 5 ml aliquots of PC were removed on days 1, 3 and 7 of storage and compared with baseline results using the in vitro parameters described in the following examples. The results using 1 gram or 2 grams of resin in either Fenwal or Cutter bags are compared to Fenwall bag controls in Tables 1 through 16. Except for slight discrepancies in the changes in platelet count and morphology scores, there are no significant differences between the Fenwal and Cutter resin bags.

EXAMPLE 2

Platelet Counts

Platelet counts were performed electronically in duplicate using a Coulter Thrombo Counter (Coulter Electronics Inc., Hialeach, Fla.). During the seven days of study, a decrease in platelet count was observed with a drop in the control bags to 85% of baseline. The initial high baseline platelet counts achieved by halving the initial volume of the platelet concentrates should be noted. A more profound drop in platelet count was noted in both the one and two gram resin bags at days 3 and 7, which was not significantly different from the controls. As can be seen in Tables 1 and 2, the fall in platelet count was not quite as rapid in the Cutter bags. Examination of the resin beads under phase microscopy did not demonstrate platelets coating the beads.

RESULT TABLE 1

RESULTS USING 1 GRAM RESIN IN FENWAL AND CUTTER BAGS COMPARED TO FENWAL CONTROL BAGS
Determination: Platelet Count ($\times 10^{12}$/L)

| Experiment No. | Initial Baseline Levels DAY 0 | CONTROL | | | FENWAL | | | CUTTER | | |
|---|---|---|---|---|---|---|---|---|---|---|
| | | DAY 1 | DAY 3 | DAY 7 | DAY 1 | DAY 3 | DAY 7 | DAY 1 | DAY 3 | DAY 7 |
| 1 | 3.8 | 3.8 | 3.0 | 3.0 | 3.4 | 2.3 | 1.1 | 3.8 | 3.2 | 1.9 |
| 2 | 3.0 | 3.1 | 2.2 | 2.4 | 2.9 | 2.3 | 1.7 | 3.0 | 2.6 | 2.0 |
| 3 | 3.0 | 3.6 | 3.0 | 2.9 | 3.2 | 2.2 | 1.4 | 3.3 | 2.8 | 2.0 |
| x̄ | 3.3 | 3.5 | 2.7 | 2.8 | 3.2 | 2.3 | 1.4 | 3.4 | 2.9 | 2.0 |
| SD | 0.5 | 0.4 | 0.5 | 0.3 | 0.9 | 0.06 | 0.3 | 0.4 | 0.3 | 0.06 |
| SE | 0.3 | 0.2 | 0.3 | 0.2 | 0.5 | 0.03 | 0.2 | 0.2 | 0.2 | 0.03 |

RESULT TABLE 2

RESULTS USING 2 GRAM RESIN IN FENWAL AND CUTTER BAGS COMPARED TO FENWAL CONTROL BAGS
Determination: Platelet Count ($\times 10^{12}$/L)

| Experiment No. | Initial Baseline Levels DAY 0 | CONTROL | | | FENWAL | | |
|---|---|---|---|---|---|---|---|
| | | DAY 1 | DAY 3 | DAY 7 | DAY 1 | DAY 3 | DAY 7 |
| 4 | 3.0 | 3.6 | 3.0 | 2.0 | 2.7 | 1.7 | 1.6 |
| 5 | 4.1 | 4.3 | 3.1 | 3.4 | 3.5 | 2.3 | 1.5 |
| 6 | 3.7 | 4.3 | 3.2 | 4.0 | 3.8 | 2.0 | 1.7 |
| x̄ | 3.6 | 4.1 | 3.1 | 3.1 | 3.3 | 2.0 | 1.6 |
| SD | 0.6 | 0.4 | 0.1 | 1.0 | 0.6 | 0.3 | 0.1 |

RESULT TABLE 2-continued
RESULTS USING 2 GRAM RESIN IN FENWAL
AND CUTTER BAGS COMPARED TO
FENWAL CONTROL BAGS
Determination: Platelet Count ($\times 10^{12}$/L)

| Experiment No. | Initial Baseline Levels DAY 0 | CONTROL DAY 1 | DAY 3 | DAY 7 | FENWAL DAY 1 | DAY 3 | DAY 7 |
|---|---|---|---|---|---|---|---|
| SE | 0.3 | 0.2 | 0.1 | 0.6 | 0.3 | 0.2 | 0.1 |

EXAMPLE 3 pH Determinations

Within 24 hours of storage at high concentration the pH in the control bags had decreased significantly and was less than 6.0 by day 3. In contrast, the one gram resin bags maintained a pH which did not differ significantly from day 0 control baseline levels even after seven days of storage. A significant increase in pH was observed using two grams of resin beginning as early as 24 hours after storage, as shown in Tables 3 and 4.

RESULT TABLE 3
RESULTS USING 1 GRAM RESIN IN FENWAL AND CUTTER BAGS
COMPARED TO FENWAL CONTROL BAGS
Determination: pH

| Experiment No. | Initial Baseline Levels DAY 0 | CONTROL DAY 1 | DAY 3 | DAY 7 | FENWAL DAY 1 | DAY 3 | DAY 7 | CUTTER DAY 1 | DAY 3 | DAY 7 |
|---|---|---|---|---|---|---|---|---|---|---|
| 1 | 6.96 | 6.21 | 5.78 | 5.75 | 7.12 | 6.90 | — | 7.27 | 6.88 | — |
| 2 | 7.24 | 6.15 | 5.87 | 5.67 | 7.00 | 6.93 | 6.94 | 7.10 | 6.87 | 6.94 |
| 3 | 7.04 | 6.49 | 5.80 | 5.83 | 7.18 | 6.91 | 7.02 | 7.08 | 6.85 | 7.04 |
| x̄ | 7.08 | 6.28 | 5.82 | 5.75 | 7.10 | 6.91 | 6.99 | 7.15 | 6.87 | 6.99 |
| SD | 0.144 | 0.181 | .047 | 0.08 | 0.092 | 0.015 | 0.044 | 0.104 | 0.015 | 0.050 |
| SE | 0.083 | 0.105 | .027 | .046 | 0.053 | 0.009 | 0.025 | 0.060 | 0.009 | .029 |

RESULT TABLE 4
RESULTS USING 2 GRAM RESIN IN FENWAL
AND CUTTER BAGS COMPARED TO
FENWAL CONTROL BAGS
Determination: pH

| Experiment No. | Initial Baseline Levels DAY 0 | CONTROL DAY 1 | DAY 3 | DAY 7 | FENWAL DAY 1 | DAY 3 | DAY 7 |
|---|---|---|---|---|---|---|---|
| 4 | 7.04 | 6.49 | 5.80 | 5.83 | 7.48 | 7.39 | 7.39 |
| 5 | 6.86 | 6.70 | 5.79 | 5.80 | 7.44 | 7.42 | 7.40 |
| 6 | 6.69 | 5.85 | 5.60 | — | 7.19 | 7.16 | — |
| x̄ | 6.86 | 6.35 | 5.73 | 5.82 | 7.37 | 7.32 | 7.40 |
| SD | .18 | .44 | .11 | 0.02 | .16 | .14 | 0.01 |
| SE | .100 | .260 | .065 | 0.009 | .091 | .082 | 0.003 |

EXAMPLE 4

Morphology Scores

Morphologic evaluation by phase microscopy was done using the scoring method described by Kunicki et al., 1975. In this method, 200 individual platelets were evaluated morphologically, scored and then totaled, with a maximum score of 400 being accorded to a preparation in which all of the platelets are normal and discoid in shape with progressively lower scores for spherical or ballooned platelets. There was a profound change in the morphology of the control cells by the third day of storage with the overwhelming majority of the cells being either ballooned or rounded with large numbers of dendritic projections. Approximately 30% of the platelets retained a normal appearing discoid configuration in the resin bags at seven days. Although the morphology scores fell in the resin bags as well, the score remained significantly better Table 5 and 6 than controls at three and seven days.

RESULT TABLE 5
RESULTS USING 1 GRAM RESIN IN FENWAL AND CUTTER BAGS
COMPARED TO FENWAL CONTROL BAGS
Determination: Morphology Score

| Experiment No. | Initial Baseline Levels DAY 0 | CONTROL DAY 1 | DAY 3 | DAY 7 | FENWAL DAY 1 | DAY 3 | DAY 7 | CUTTER DAY 1 | DAY 3 | DAY 7 |
|---|---|---|---|---|---|---|---|---|---|---|
| 1 | 400 | 400 | 200 | 148 | 400 | 276 | 188 | 400 | 317 | 218 |
| 2 | 313 | 304 | 164 | 141 | 317 | 296 | 286 | 320 | 334 | 273 |
| 3 | 367 | 287 | 146 | 165 | 368 | 322 | 247 | 358 | 348 | 233 |
| x̄ | 360 | 330.3 | 170 | 151.2 | 361.7 | 297.9 | 240.3 | 359.3 | 333 | 241.3 |
| SD | 43.9 | 60.9 | 27.5 | 12.6 | 41.9 | 23.1 | 49.3 | 40.0 | 15.5 | 28.4 |
| SE | 25.4 | 35.2 | 15.9 | 7.2 | 24.2 | 13.3 | 28.5 | 23.1 | 9.0 | 16.4 |

RESULT TABLE 6

RESULTS USING 2 GRAM RESIN IN FENWAL AND CUTTER BAGS COMPARED TO FENWAL CONTROL BAGS
Determination: Morphology Score

| Experiment No. | Initial Baseline Levels DAY 0 | CONTROL DAY 1 | CONTROL DAY 3 | CONTROL DAY 7 | FENWAL DAY 1 | FENWAL DAY 3 | FENWAL DAY 7 |
|---|---|---|---|---|---|---|---|
| 4 | 367 | 286.5 | 146 | 165 | 334.5 | 277.5 | 257 |
| 5 | 358.5 | 293.5 | 148 | 140 | 336.5 | 273.5 | 262.5 |
| 6 | 350.0 | 271 | 133.5 | 143.5 | 337.5 | 261.0 | — |
| $\bar{x}$ | 358.7 | 283.7 | 142.7 | 149.7 | 336.7 | 270.7 | 260.0 |
| SD | 8.50 | 11.80 | 7.60 | 13.40 | 1.50 | 8.90 | 3.00 |
| SE | 4.91 | 6.81 | 4.40 | 7.80 | .88 | 5.10 | 1.73 |

RESULT TABLE 8

RESULTS USING 2 GRAM RESIN IN FENWAL AND CUTTER BAGS COMPARED TO FENWAL CONTROL BAGS
Determination: ATP ($\mu$M/$10^{11}$ platelets)

| Experiment No. | Initial Baseline Levels DAY 0 | CONTROL DAY 1 | CONTROL DAY 3 | CONTROL DAY 7 | FENWAL DAY 1 | FENWAL DAY 3 | FENWAL DAY 7 |
|---|---|---|---|---|---|---|---|
| 4 | 5.869 | 5.101 | 1.270 | 0.472 | 5.395 | 4.411 | 3.496 |
| 5 | 4.840 | 4.720 | 1.176 | 0.594 | 5.235 | 3.198 | 2.798 |
| 6 | 6.082 | 3.676 | 1.280 | 0.679 | 5.552 | 3.882 | — |
| $\bar{x}$ | 5.60 | 4.50 | 1.24 | .582 | 5.40 | 3.83 | 3.15 |
| SD | .66 | .74 | .057 | .104 | .16 | .61 | .349 |
| SE | .38 | .43 | .033 | .060 | .091 | .35 | .202 |

EXAMPLE 5

ATP Content

Total ATP content was determined as described by Bucher using a phosphoglycerate kinase-glyceraldehyde phosphate dehydrogenase enzyme-coupled system (Sigma Chemicals, St. Louis, Mo.). The amount of total ATP/$10^{11}$ platelets decreased to approximately 80% after 24 hours, to 16% after three days and to 10% of baseline after seven days of storage in control preparations. In contrast, there was no significant fall in the ATP levels in the one gram resin (Table 7) bags until seven days of storage and in these bags the total ATP content was still approximately 60% that of baseline. The results using two grams of resin (Table 8) were similar to the one gram resin results.

EXAMPLE 6

Thrombin Induced Release of Adenine Nucleotide

Aliquots of the platelet concentrate were washed twice with EDTA-TRIS saline buffer (pH 7.4) and their total adenine nucleotide release after stimulation with 0.06 NIH units of thrombin/ml (Sigma Chemicals) was assayed as previously described by Murer, 1968. After 24 hours of preservation of control platelets, only 45% of baseline thrombin induced release was noted. Thrombin induced release was also decreased in all of the resin bags by 24 hours although the fall was not significant in the one gram Fenwal bags, yielding 64% of baseline values. There was no significant decrease in Thrombin induced release in the Cutter one gram bag in comparison with baseline levels. No release was observed after

RESULT TABLE 7

RESULTS USING 1 GRAM RESIN IN FENWAL AND CUTTER BAGS COMPARED TO FENWAL CONTROL BAGS
Determination: ATP ($\mu$M/$10^{11}$ platelets)

| Experiment No. | Initial Baseline Levels DAY 0 | CONTROL DAY 1 | CONTROL DAY 3 | CONTROL DAY 7 | FENWAL DAY 1 | FENWAL DAY 3 | FENWAL DAY 7 | CUTTER DAY 1 | CUTTER DAY 3 | CUTTER DAY 7 |
|---|---|---|---|---|---|---|---|---|---|---|
| 1 | 5.253 | 4.264 | 0.622 | 0.776 | 5.881 | 3.802 | 2.877 | 5.250 | 3.538 | 2.935 |
| 2 | 6.031 | 4.686 | 0.883 | 0.558 | 5.876 | 4.871 | 3.795 | 5.797 | 5.082 | 3.851 |
| 3 | 5.869 | 5.101 | 1.270 | 0.472 | 5.308 | 5.621 | 2.258 | 6.138 | 4.399 | 3.496 |
| $\bar{x}$ | 5.717 | 4.684 | 0.925 | 0.602 | 5.688 | 4.764 | 2.977 | 5.728 | 4.339 | 3.455 |
| SD | .410 | .419 | .326 | .157 | .329 | 0.914 | .773 | .448 | .774 | .459 |
| SE | .237 | .242 | .188 | .091 | .190 | 0.528 | .446 | .259 | .447 | .265 |
| % of Control | 100% | 81.9% | 16.2% | 10.7% | 99.3% | 77.5% | 52.9% | 100.1% | 75.9% | 59.8% | three days of storage in either the control or resin bags. The results are summarized in Tables 9 and 10.

RESULT TABLE 9

RESULTS USING 1 GRAM RESIN IN FENWAL AND CUTTER BAGS COMPARED TO FENWAL CONTROL BAGS
Determination: Nucleotide Release ($\mu$M/$10^{11}$ platelets)

| Experiment No. | Initial Baseline Levels DAY 0 | CONTROL DAY 1 | CONTROL DAY 3 | CONTROL DAY 7 | FENWAL DAY 1 | FENWAL DAY 3 | FENWAL DAY 7 | CUTTER DAY 1 | CUTTER DAY 3 | CUTTER DAY 7 |
|---|---|---|---|---|---|---|---|---|---|---|
| 1 | 4.375 | 3.192 | 0.00 | — | 3.142 | 0.00 | — | 3.182 | 0.00 | — |
| 2 | 4.751 | 1.732 | 0.513 | — | 2.659 | 2.264 | — | 4.964 | 1.475 | — |
| 3 | 5.102 | 1.585 | 0.00 | — | 3.136 | 0.00 | — | 3.731 | 0.00 | — |
| $\bar{x}$ | 4.743 | 2.17 | 0.171 | — | 2.979 | .755 | — | 3.959 | .492 | — |
| SD | .364 | 0.888 | .296 | — | .277 | 1.307 | — | .913 | .852 | — |
| SE | .210 | .514 | .17 | — | .160 | .755 | — | .527 | .492 | — |

RESULT TABLE 10

RESULTS USING 2 GRAM RESIN IN FENWAL AND CUTTER BAGS COMPARED TO FENWAL CONTROL BAGS

Determination: Nucleotide Release ($\mu M/10^{11}$ platelets)

| Experiment | Initial Baseline Levels | CONTROL | | | FENWAL | | |
|---|---|---|---|---|---|---|---|
| No. | DAY 0 | DAY 1 | DAY 3 | DAY 7 | DAY 1 | DAY 3 | DAY 7 |
| 4 | 5.102 | 1.585 | 0.00 | — | 4.144 | 0.00 | — |
| 5 | 3.961 | 3.496 | 0.00 | — | 3.436 | 0.00 | — |
| 6 | 3.748 | 0.599 | 0.00 | — | 3.030 | 0.00 | — |
| x̄ | 4.27 | 1.90 | 0.00 | — | 3.536 | 0.00 | — |
| SD | .73 | 1.47 | 0.00 | — | .564 | 0.00 | — |
| SE | .42 | 0.85 | 0.00 | — | .326 | 0.00 | — |

EXAMPLE 7

Acid and Gas Analysis pH, $PO_2$, $PCO_2$, and $HCO_3$ were estimated using a Corning 165 Blood Gas Analyzer. The pH was measured at 37° and temperature conversion to 22° was calculated using conventional procedures. The $pO_2$ in the control bags was 0 during the first 24 hours of storage and then rose after the third and seventh day of platelet preservation. The addition of one or two grams of resin maintained the low $pO_2$ level during three days of storage with a rise occuring only on the seventh day Table when the $pO_2$ reached approximately 50% of the amount observed in control bags in both the one and two gram resin bags.

The $pCO_2$ rose during the first 24 hours of storage in the control bags and then began to decrease, almost reaching 0 mm Hg by day seven. In the resin bags $pCO_2$ remained at physiological plasma levels and rose slightly after 3 days of storage. By the seventh day of storage $pCO_2$ levels were approximately 50% lower than day 1 values in Fenwal resin bags. $pCO_2$ levels in Cutter resin bags returned to day 1 values at the seventh day of storage.

$HCO_3$ was depleted to zero during seven days of storage in control bags. In contrast, $HCO_3$ levels remained between 30 and 60% of controls at day seven in the one and two gram resin bags respectively. The results are shown in Tables 11 through 16.

RESULT TABLE 11

RESULTS USING 1 GRAM RESIN IN FENWAL AND CUTTER BAGS COMPARED TO FENWAL CONTROL BAGS

Determination: $PO_2$ (mm Hg)

| Experiment | Initial Baseline Levels | CONTROL | | | FENWAL | | | CUTTER | | |
|---|---|---|---|---|---|---|---|---|---|---|
| No. | DAY 0 | DAY 1 | DAY 3 | DAY 7 | DAY 1 | DAY 3 | DAY 7 | DAY 1 | DAY 3 | DAY 7 |
| 1 | 0 | 0 | 73 | 126 | 0 | 4 | 0 | 0 | 0 | 0 |
| 2 | 0 | 0 | 61 | 127 | 0 | 0 | 3.5 | 0 | 1 | 0 |
| 3 | 0 | 0 | 71 | 135 | 0 | 0 | 82 | 0 | 0 | 58.5 |
| x̄ | 0.0 | 0.0 | 68.3 | 129.3 | 0.0 | 1.3 | 28.5 | 0.0 | .33 | 19.5 |
| SD | 0.0 | 0.0 | 6.43 | 4.93 | 0.0 | 2.3 | 46.4 | 0.0 | .58 | 33.8 |
| SE | 0.0 | 0.0 | 3.71 | 2.85 | 0.0 | 1.3 | 26.8 | 0.0 | .33 | 19.5 |

RESULT TABLE 12

RESULTS USING 2 GRAM RESIN IN FENWAL AND CUTTER BAGS COMPARED TO FENWAL CONTROL BAGS

Determination: $PO_2$ (mm Hg)

| Experiment | Initial Baseline Levels | CONTROL | | | FENWAL | | |
|---|---|---|---|---|---|---|---|
| No. | DAY 0 | DAY 1 | DAY 3 | DAY 7 | DAY 1 | DAY 3 | DAY 7 |
| 1 | 0 | 0 | 71.0 | 135 | 0 | 7 | 5.24 |
| 2 | 0 | 0 | 26.0 | 138 | 0 | 0.0 | 59.0 |
| 3 | 0 | 0 | 6.0 | 129 | 0 | 0.0 | 62.0 |
| x̄ | 0 | 0 | 34.3 | 134.0 | 0 | 2.3 | 42.1 |
| SD | 0 | 0 | 33.3 | 4.58 | 0 | 4.0 | 31.9 |
| SE | 0 | 0 | 19.2 | 2.65 | 0 | 2.3 | 18.4 |

RESULT TABLE 13

RESULTS USING 1 GRAM RESIN IN FENWAL AND CUTTER BAGS COMPARED TO FENWAL CONTROL BAGS

Determination: $PCO_2$ (mm Hg)

| Experiment | Initial Baseline Levels | CONTROL | | | FENWAL | | | CUTTER | | |
|---|---|---|---|---|---|---|---|---|---|---|
| No. | DAY 0 | DAY 1 | DAY 3 | DAY 7 | DAY 1 | DAY 3 | DAY 7 | DAY 1 | DAY 3 | DAY 7 |
| 1 | 77.3 | 132 | 50 | 14 | 33 | 46 | 43 | 26 | 41 | 46 |
| 2 | 82.2 | 94.0 | 40 | 9.0 | 30 | 47 | 40 | 28 | 55 | 44 |
| 3 | 57.1 | 93.9 | 20 | 2.0 | 29.2 | 37.8 | 16.7 | 26.3 | 36.5 | 25.5 |
| x̄ | 72.2 | 106.6 | 36.7 | 8.3 | 30.7 | 43.6 | 33.2 | 26.8 | 44.17 | 38.5 |
| SD | 13.3 | 21.97 | 15.3 | 6.0 | 2.0 | 5.0 | 14.4 | 1.1 | 9.65 | 11.3 |
| SE | 7.7 | 12.69 | 8.8 | 3.5 | 1.2 | 2.9 | 8.3 | 0.6 | 5.57 | 6.5 |

RESULT TABLE 14

RESULTS USING 2 GRAM RESIN IN FENWAL AND CUTTER BAGS COMPARED TO FENWAL CONTROL BAGS
Determination: $PCO_2$ (mm Hg)

| Experiment No. | Initial Baseline Levels DAY 0 | CONTROL | | | FENWAL | | |
|---|---|---|---|---|---|---|---|
| | | DAY 1 | DAY 3 | DAY 7 | DAY 1 | DAY 3 | DAY 7 |
| 1 | 57.1 | 93.9 | 20.0 | 1.9 | 10.3 | 12.9 | 14.3 |
| 2 | 82.2 | 92.4 | 43.6 | 3.0 | 8.60 | 11.9 | 14.8 |
| 3 | 67.4 | 119.5 | 67.4 | 2.0 | 10.9 | 14.2 | 20.1 |
| x̄ | 68.9 | 101.9 | 43.7 | 2.3 | 9.93 | 13.0 | 16.4 |
| SD | 12.6 | 15.2 | 23.7 | 0.61 | 1.19 | 1.15 | 3.21 |
| SE | 7.29 | 8.80 | 13.7 | 0.35 | 0.69 | 0.67 | 1.86 |

RESULT TABLE 15

RESULTS USING 1 GRAM RESIN IN FENWAL AND CUTTER BAGS COMPARED TO FENWAL CONTROL BAGS
Determination: $HCO_3$ (mM/L)

| Experiment No. | Initial Baseline Levels DAY 0 | CONTROL | | | FENWAL | | | CUTTER | | |
|---|---|---|---|---|---|---|---|---|---|---|
| | | DAY 1 | DAY 3 | DAY 7 | DAY 1 | DAY 3 | DAY 7 | DAY 1 | DAY 3 | DAY 7 |
| 1 | 11.0 | 3.0 | 0 | 0 | 7.0 | 5.0 | 6.0 | 8.0 | 6.0 | 6.0 |
| 2 | 10.6 | 4.5 | 1 | 0 | 6.9 | 6.0 | 6.0 | 7.2 | 7.0 | 6.0 |
| 3 | 10.1 | 4.8 | 0 | 0 | 6.4 | 5.0 | 3.3 | 6.9 | 5.2 | 4.5 |
| x̄ | 10.6 | 4.1 | 0.33 | 0 | 6.8 | 5.3 | 5.1 | 7.37 | 6.1 | 5.5 |
| SD | 0.45 | 0.96 | 0.58 | 0 | 0.32 | 0.58 | 1.6 | 0.57 | .90 | 0.9 |
| SE | 0.26 | 0.56 | 0.33 | 0 | 0.19 | 0.33 | 0.9 | 0.33 | .52 | 0.5 |

RESULT TABLE 16

RESULTS USING 2 GRAM RESIN IN FENWAL AND CUTTER BAGS COMPARED TO FENWAL CONTROL BAGS
Determination: $HCO_3$ (mM/L)

| Experiment No. | Initial Baseline Levels DAY 0 | CONTROL | | | FENWAL | | |
|---|---|---|---|---|---|---|---|
| | | DAY 1 | DAY 3 | DAY 7 | DAY 1 | DAY 3 | DAY 7 |
| 1 | 10.1 | 4.8 | 0 | 0 | 5.0 | 5.0 | 5.3 |
| 2 | 9.5 | 7.6 | 0 | 0 | 3.9 | 4.8 | 5.6 |
| 3 | 8.1 | 2.2 | 1.9 | 1.5 | 3.7 | 4.7 | 4.9 |
| x̄ | 9.2 | 4.9 | 0.6 | 0.5 | 4.2 | 4.8 | 5.3 |
| SD | 1.03 | 2.70 | 1.10 | 0.87 | 0.70 | 0.15 | 0.35 |
| SE | 0.59 | 1.56 | 0.63 | 0.5 | 0.40 | 0.09 | 0.20 |

EXAMPLE 8

Electron Microscopy

Platelets were obtained after 0, 1, 3 and 7 days of storage in 1 gram resin bags and controls fixed in 4% formaldehyde, 1% gluteraldehyde, in a 1:1 ratio at 4° C. for 4–6 hours. The samples were washed in sucrose buffer (0.2 M. sucrose in 0.1 M s-collidine). The samples were post fixed in 2% osmium tetroxide buffered with 0.1 M s-collidone) for 90 minutes. Prior to dehydration tissues were stained en blanc with uranyl acetate for 1 hour. Platelets were dehydrated through a graded series of ethanol mixtures, 35%, 70%, 95%, absolute (2 times) and propylene oxide (2 times) for 30 minutes each time. Platelets were then infiltrated with a mixture of 50% propylene oxide and Epon for 1 hour. Platelets were then infiltrate into a mixture of 70% Epon: 30% propylene oxide for 24 hours, embedded and polymerized at a temperature of 60° C. for 48 hours. Toluidine blue-stained 0.5 um Epon sections were prepared for light microscopy to select the areas for cutting thin sections for electron microscopy. Thin sections were double-stained with uranyl acetate and lead citrate and examined in a JEOL 100B electrton microscope.

Figure 1:
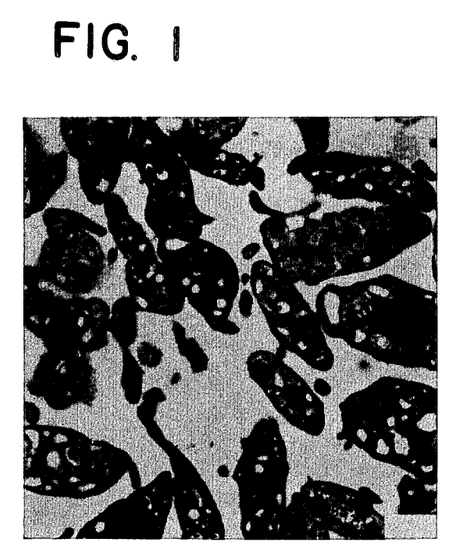
FIG. 1 shows Day 0 platelets at initiation of the experiment. The platelets are normal ultrastructurally and almost 100% discoid. TEM×3,000.
Figure 2:
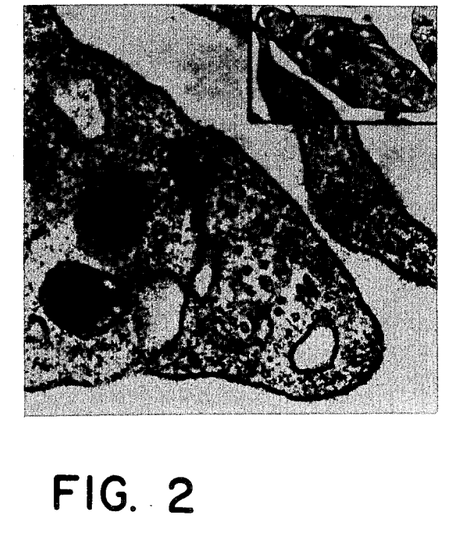
FIG. 2 shows Day 3 platelets preserved with resin in Cutter transfer bags (CL-3000). Definite microtubules are seen in many of the platelets as demonstrated by this enlargement of peripheral microtubules encircles in black in the cell in the upper right corner. TEM×20,000.
Figure 3:
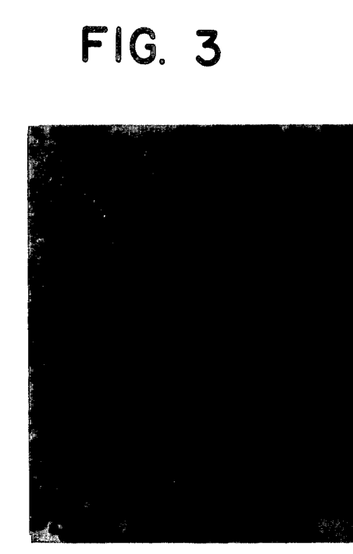
FIG. 3 shows Day 1 control platelets. Most control platelets have lost their discoid appearance and are rounded in shape with multiple dendritic projections. Loss of dense granules is evident. TEM×3,000.
Figure 4:
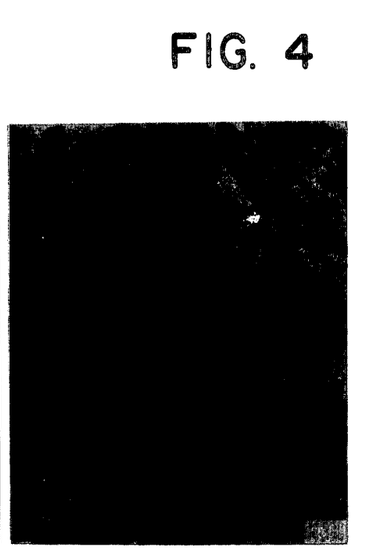
FIG. 4 shows Day 1 platelets stored with resin in Cutter transfer bags (CL-3000). Most of the platelets are normal ultrastructurally, with the majority discoid. TEM×3,000.
Figure 5:
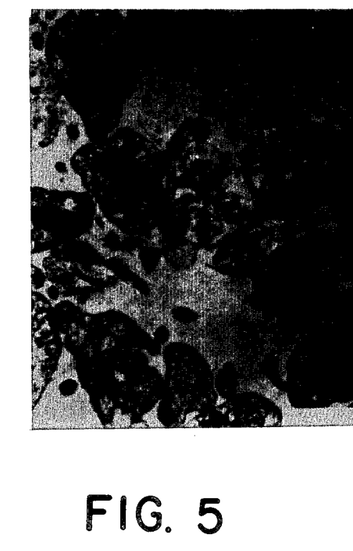
FIG. 5 shows Day 3 control platelets. Most control platelets are grossly abnormal with evidence of marked degranulation and obvious fragmentation. Cell membrane breakage is also noted and many platelets appear non-viable, with no discoid platelets remaining. TEM×3,000.
Figure 7:
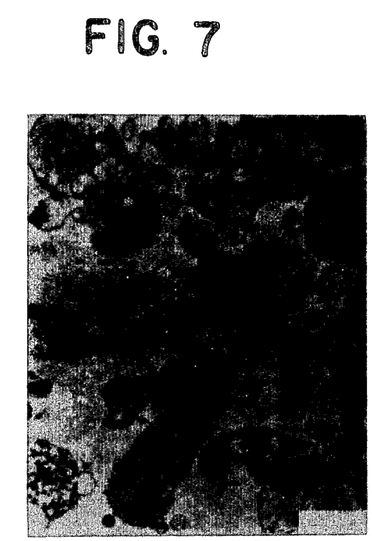
FIG. 7 shows Day 4 control platelets. Further deterioration has occurred with no viable platelets seen. Obvious indications of irreversible cell injury are noted with matrical densities in remaining mitochondria (center left border) and bleb formation (center) indicative of membrane injury. TEM.×3,000.

By day 3 in double platelet concentrates, the control platelets illustrated morphology features commonly observed to occur with platelet senescence. The platelets appear to be smaller and less dense and have lost the majority of their dense granules, indicating loss of the release reaction. Loss of shape was substantiated by the numerous irregular contours and absence of microtubules. Nearly total degranulation was observed by the third day of storage of the control double PC. In contrast, double PC stored with resin in both the Fenwal and Cutter bags maintained their shape in the majority of platelets seen. Dense granules were plentiful and microtubules were still present. By day 3 in the double PC controls, platelets appear swollen, pale, spherical, and exhibit broken plasma membranes. Flocculant matrical densities are observed in the mitochondria indicating lethal cell injury as has been described by Trump et al. for other tissue cell models.

Figure 6:
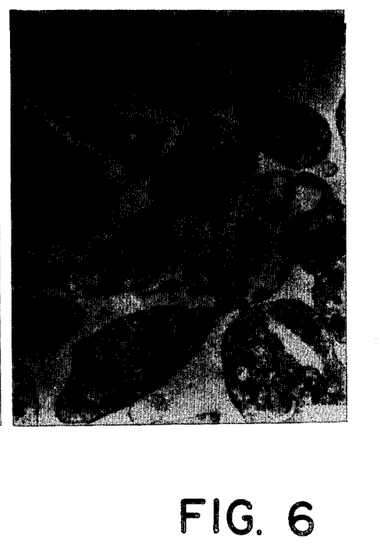
FIG. 6 shows Day 3 platelets preserved with resin, which remain discoid with near normal numbers of granules in most platelets. Partially degranulated platelets (center and upper right) are occasionally seen. TEM×3,000.
Figure 8:
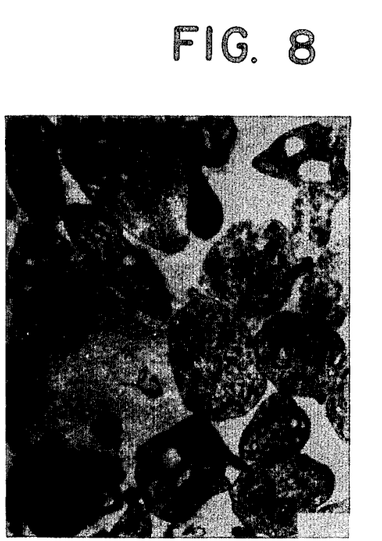
FIG. 8 shows Day 4 platelets stored with resin. Loss of discoid shape is noted in some platelets, although a considerable number of intact platelets remain. Several degranulated platelets are seen. TEM×3,000.
Figure 9:
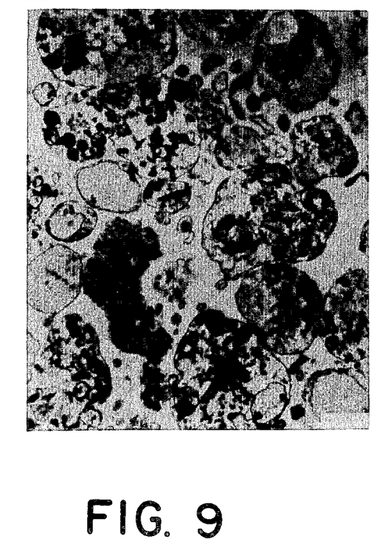
FIG. 9 shows Day 7 control platelets. 100% non-viable platelets are seen with total degranulation and large amounts of cellular debris. TEM×3,000.
Figure 10:
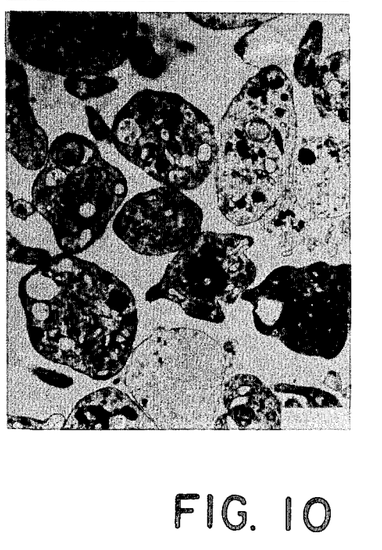
FIG. 10 shows Day 7 platelets stored with resin exhibiting obvious degranulation and loss of discoid shape, although a considerable number of intact platelets remain. TEM×4,000.

In contrast, platelets stored in the resin bags for three and seven days maintained their shape. Although pseudopod formation was evident, dense granules were still numerous and microtubules were present. The amount of disc-to-sphere transformation was minimal. Post-transfusion platelet survival has been positively correlated with the amount of disc-to-sphere transformation. Double platelet concentrates stored with resin still maintained shape even after seven days of storage, with morphology scores around 240. The morphology of the resin platelets was clearly better preserved than the virtually 100% non-viable control platelets after seven days of room temperature storage.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

As can be seen from the present specification and examples, the present invention is industrially useful in providing a means for extending the shelf life of blood leukocytes or platelets stored in vivo in accordance with the present invention.

What is claimed is:

1. In a composition of matter consisting essentially of metabolizing leukocytes or platelets in an in vitro environment capable of supporting platelet metabolism, the improvement which comprises a water-insoluble polymer containing releasable phosphate or bicarbonate ions for supplying a physiologically acceptable, continuous, sustained release source of buffer to said platelets in an amount sufficient to maintain both pH and ATP levels equal to at least 60% of those of freshly prepared platelets for a storage period of at least 7 days of storage at 22° C.

2. A composition according to claim 1, wherein said environment includes packed platelets substantially free of leukocytes.

3. A composition according to claim 2 wherein said environment includes packed platelets substantially free of erythocytes.

4. A composition according to claim 1 wherein said water-insoluble polymer is particulate.

5. A composition according to claim 4, wherein said polymer is an ion exchange resin.

6. A composition according to claim 5, wherein said polymer is a weakly basic anion exchange resin.

7. A composition according to claim 6 wherein said buffer is inorganic dibasic phosphate $HPO_4^{--}$.

8. A composition according to claim 7 wherein said platelets are human platelets.

9. A composition according to claim 7 wherein said in vitro environment is within a sterile platelet collection container.

10. In an article of manufacture comprising a sterile platelet collection and storage container, the improvement which comprises a water-insoluble polymer containing releaseable phosphate or bicarbonate ions for supplying a continuous, sustained release source of buffer to metabolizing leukocytes or platelets in an amount sufficient to maintain both pH and ATP levels of said leukocytes or platelets at least equal to 60% of those levels in freshly prepared cells for a storage period equivalent to at least 7 days of storage at 22° C.

11. An article according to claim 10 wherein said water insoluble polymer is particulate.

12. An article according to claim 11, wherein said polymer is an ion-exchange resin.

13. An article according to claim 12, wherein said polymer is a weakly basic anion exchange resin.

14. In a method for maintaining metabolizing leukocytes or platelets suitable for transfusion in a sterile container, the improvement which comprises added to said container a water-insoluble polymer containing releasable phosphate or bicarbonate ions for supplying a continuous source of buffer to said metabolizing cells in an amount sufficient to maintain both pH and ATP levels equal to at least 60% of those levels in freshly prepared cells for a storage period equivalent to at least 7 days of storage at 22° C.

15. A method according to claim 14 wherein said water-insoluble polymer is particulate.

16. A method according to claim 15 wherein said polymer is an ion exchange resin.

17. A method according to claim 16 wherein said polymer is a weakly basic anion exchange resin.

18. A storable, transfusable composition of matter comprising metabolizing leukocytes or platelets in an in vitro environment substantially free of erythrocytes and capable of supporting cellular metabolism having incorporated therein a water-insoluble polymer containing releasable phosphate or bicarbonate ions capable of continuously supplying weakly basic buffer to said cells.

19. A composition according to claim 18 wherein said water-insoluble polymer is particulate.

20. A composition according to claim 19 wherein said polymer is an ion exchange resin.

* * * * *